United States Patent [19]

Green et al.

[11] Patent Number: 5,156,614
[45] Date of Patent: Oct. 20, 1992

[54] APPARATUS FOR APPLYING TWO-PART SURGICAL FASTENERS

[75] Inventors: David T. Green, Westport; Henry Bolanos, East Norwalk; Robert J. Geiste, Milford, all of Conn.; Wayne P. Young, Brewster, N.Y.; Stephen W. Gerry, Bethel; Frank M. Rende, III, Stamford, both of Conn.

[73] Assignee: United States Surgical Corporation, Norwalk, Conn.

[21] Appl. No.: 794,596

[22] Filed: Nov. 14, 1991

Related U.S. Application Data

[63] Continuation of Ser. No. 583,867, Sep. 17, 1990, abandoned.

[51] Int. Cl.5 .............................................. A61B 17/00
[52] U.S. Cl. .................................. 606/220; 227/176; 227/178; 227/180
[58] Field of Search ........... 606/220; 227/19, 175-182

[56] References Cited

U.S. PATENT DOCUMENTS

| | | |
|---|---|---|
| 3,079,606 | 3/1963 | Bobrov et al. |
| 3,490,675 | 1/1970 | Green et al. |
| 3,499,591 | 3/1970 | Green |
| 3,844,289 | 10/1974 | Noiles |
| 4,086,926 | 5/1978 | Green et al. |
| 4,204,623 | 5/1980 | Green |
| 4,256,251 | 3/1981 | Moshoisky ............................ 227/19 |
| 4,354,628 | 10/1982 | Green |
| 4,391,401 | 7/1983 | Mosholsky ........................... 227/19 |
| 4,429,695 | 2/1984 | Green ................................. 227/180 |
| 4,473,077 | 9/1984 | Noiles et al. ........................ 227/19 |
| 4,506,670 | 3/1985 | Crossley ............................ 227/175 |
| 4,520,817 | 6/1985 | Green |
| 4,576,165 | 3/1986 | Green et al. |
| 4,576,167 | 3/1986 | Noiles ................................. 227/19 |
| 4,589,416 | 5/1986 | Green |
| 4,597,517 | 7/1986 | Wagdy .................................. 227/8 |
| 4,606,345 | 8/1986 | Dorband et al. |
| 4,608,981 | 9/1986 | Rothfuss et al. ..................... 227/180 |
| 4,633,861 | 1/1987 | Chow et al. ......................... 227/180 |
| 4,633,874 | 1/1987 | Chow et al. ......................... 227/180 |
| 4,664,305 | 5/1987 | Blake, III et al. .................... 227/19 |
| 4,665,916 | 5/1987 | Green ................................. 227/178 |
| 4,809,898 | 3/1989 | Gassner et al. ........................ 227/8 |
| 4,863,088 | 9/1989 | Redmond et al. ..................... 227/19 |
| 4,881,544 | 11/1989 | Green et al. |
| 4,892,244 | 1/1990 | Fox et al. .............................. 227/8 |
| 4,932,960 | 6/1990 | Green et al. ......................... 606/220 |
| 4,955,959 | 9/1990 | Tompkins et al. .................. 227/178 |

Primary Examiner—Stephen C. Pellegrino
Assistant Examiner—Gary Jackson
Attorney, Agent, or Firm—Peter G. Dilworth; Rocco S. Barrese; Thomas R. Bremer

[57] ABSTRACT

Apparatus for applying at least one row of two-part surgical fasteners to body tissue, each surgical fastener having a pronged fastener portion for piercing body tissue, and an aperture retainer dimensioned and configured for engaged reception of the pronged fastener portion in interference fit therewith for gripping the body tissue therebetween. The apparatus includes means for holding a plurality of the fastener portions in generally aligned relation, means spaced from the fastener portion holding means for gripping body tissue therebetween and for releasably holding a plurality of the retainers in generally aligned relation and positioned opposite the fasteners when the body tissue is positioned therebetween. Means is provided for sequentially advancing the pronged fastener portions toward the apertured retainers to cause the fastener portions to pierce the body tissue and to be received within the apertures of the retainers in engaged interference relation so as to cause the fastener portions and the retainers to be engaged while gripping the body tissue therebetween. In the preferred embodiment a knife edge is provided to cut the body tissue midway between opposed pairs of rows of the fasteners as the fasteners are applied. A method for applying two spaced apart pairs of rows of the fasteners to body tissue on the apparatus of the invention is also disclosed.

43 Claims, 14 Drawing Sheets

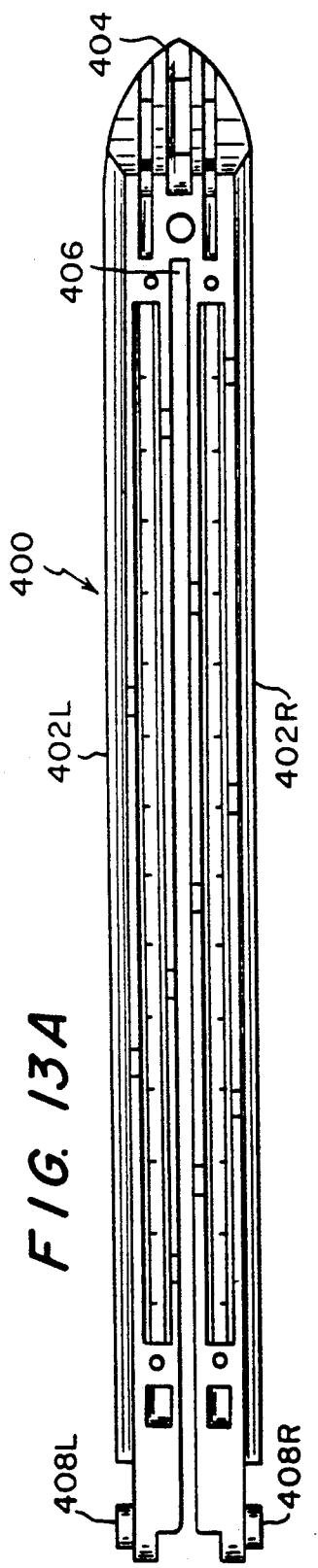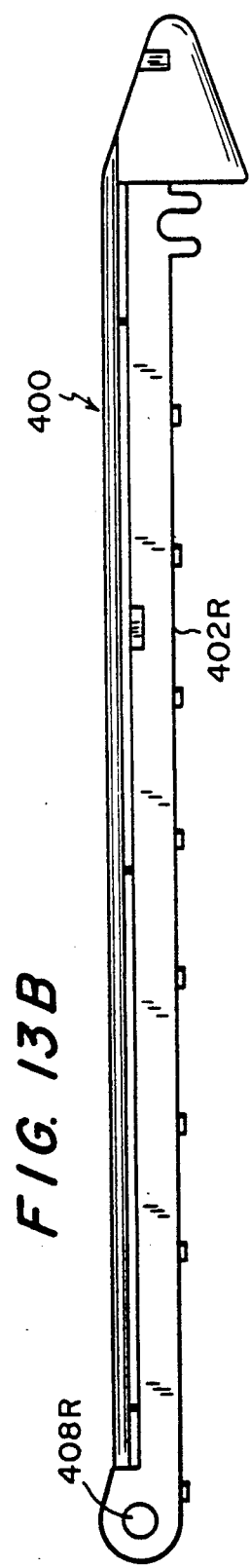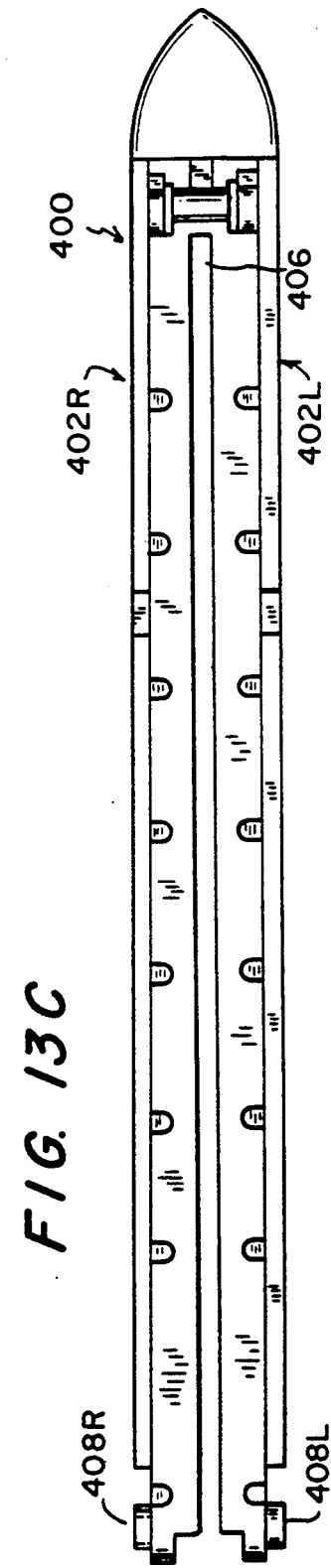

APPARATUS FOR APPLYING TWO-PART SURGICAL FASTENERS

This is a continuation of copending application Ser. No. 07/583,867 filed on Sep. 17, 1990, now abandoned.

BACKGROUND OF THE INVENTION

1. Field of the Invention

This invention relates to an apparatus for applying surgical fasteners and more particularly, to a fastener applying apparatus having an improved fastener cartridge and holder for the retainer portion of two-part surgical fasteners.

2. Background of the Prior Art

In some surgical operations it is necessary to adjoin two hollow body organs alongside each other, with their longitudinal axes positioned generally parallel to each other, and to effect a longitudinal cut through the contacting circumferential walls of the two organs in order to open them to each other. After joining the two organs they essentially constitute a single hollow chamber along the length of the cut. Correspondingly, the circumferential portions of the two adjoining organs on each lateral side of the cut must be sutured by at least one line of "stitches" in order to maintain the integrity of the union.

Instruments for this purpose are known in the art, and are described in U.S. Pat. Nos. 3,079,606, 3,490,675 and 3,499,591. Such instruments are generally referred to as linear cutting staplers and include two elongate fingers which are respectively insertable into each organ from an open end thereof such that the two fingers have the adjoining walls of the adjacent organs therebetween. Further examples of such instruments are disclosed in commonly assigned U.S. Pat. Nos. 4,429,695 and 4,520,817. The disclosures of these two last mentioned patents are incorporated herein by reference.

One of the fingers includes a disposable cartridge carrying a plurality of staples arranged in at least two lateral rows while the other finger includes an anvil for curling the staple legs into hook form upon being driven against the anvil. The stapling operation is effected by a pusher device which travels longitudinally along the cartridge carrying finger extending into one organ. The pusher mechanism acts simultaneously upon the staples at corresponding longitudinal positions in each lateral row, but successively acts upon the staples along the rows. For example, if two laterals rows of staples are provided, each row comprising twenty staples, the pusher means acts upon two staples at a time, one in each row, and successively acts upon each succeeding pair of staples.

Immediately behind the pusher means and laterally positioned between the staple rows is a knife member which severs the facing adjoining walls of the two organs to thereby longitudinally open the two organs to each other between the rows of staples.

Up to the present these devices were limited to applying metal staples. Two-part absorbable fasteners, such as those used in devices described in U.S. Pat. No. 4,665,916, hereby incorporated by reference, have been limited to devices which apply all of the fasteners simultaneously. Indeed, the retainer members of such absorbable fastener devices typically have been constructed as a web of retainers interconnected by flexible or frangible members. See, for example, U.S. Pat. No. 4,589,416. Devices of the type shown in the aforementioned U.S. Pat. Nos. 3,079,606; 3,490,675 and 3,499,591, on the other hand, employ an actuating cam bar which travels substantially perpendicularly to the direction of fastener motion to effect sequential placement of staples.

Up to the present, applying two-part absorbable fasteners with instruments of the type disclosed in U.S. Pat. Nos. 3,079,606; 3,490,675 and 3,499,591 has not been possible due in part to the peculiar difficulties inherent in aligning the separate fasteners and retainers. The present invention relates to an apparatus which successfully combines a system of applying such fasteners sequentially while cutting the tissue and effecting complete closures.

SUMMARY OF THE INVENTION

An apparatus is disclosed for applying at least one row of two-part surgical fasteners, each surgical fastener having a pronged fastener portion and a retainer, which comprises means for holding the fastener portions of the two part surgical fasteners, a retainer cartridge having means for holding a plurality of retainers in positions opposite the fastener portions, a plurality of retainer mounting elements located in the retainer cartridge for releasably engaging and holding the retainers. The fastener portions and retainers are arranged in longitudinal alignment with the axis of the apparatus, and the fastener portions are sequentially driven into engagement with their respective retainers, and means for sequentially driving the fastener portions of the two part fasteners into engagement with the respective opposed retainers.

The retainer mounting elements are slidably mounted within a lower channel in the retainer cartridge and arranged to release their respective retainers in response to the engagement of the fastener portions with their respective retainers. Further, the retainer mounting elements each comprise a base portion and at least one upright post for engaging an aperture in the retainer and frictionally holding the retainer. A surface portion of the upright post is preferably inclined on at least one vertical side and backstop means is provided for bracing the retainers when engaging with the fastener portions. The backstop means comprises a horizontal shelf portion of the cartridge upon which the retainers at least partially rest. The lower and upper channels have vertical side walls, and the lower channel is of lesser width than the upper channel and is located below the upper channel thereby forming at least one shelf portion. The lower channel has a plurality of vertical guide rails and the retainer mounting elements each have at least one vertical notch for cooperating with a respective one of the vertical guide rails. Preferably the two-part surgical fasteners are bio-absorbable and the apparatus is adapted to fasten body tissue therewith.

The preferred embodiment of the apparatus comprises a two part frame having separable sections capable of releasable attachment to each other and each having an elongated finger portion. A fastener carrying cartridge is mounted along one of the finger portions and carries a plurality of the fastener portions, and a retainer carrying cartridge is mounted along the other finger portion opposite the fastener cartridge and carries a plurality of the retainer members positioned opposite the fastener portions. A pair of cam bars is positioned for slidable movement distally and proximally within the frame for sequential engagement with the fastener pushers.

A generally U-shaped shoe plate is provided between each fastener and retainer cartridge and the respective channel members of the frame. Each shoe plate defines a channel for reception of a respective shoe associated with the cam bars. The respective shoes prevent separation of the frame members when the cam bars are advanced a predetermined distance due to the entry of said shoes associated therewith into the channels defined by the shoe plates.

A method is disclosed for applying at least one row of two-part surgical fasteners, each surgical fastener having a pronged fastener portion and a retainer, comprising, holding the fastener portions of the two-part surgical fasteners, releasably holding a plurality of retainers in positions opposite the fastener portions, and sequentially driving the fastener portions of the two-part fasteners into engagement with their respective opposed retainers. Each surgical fastener has a pronged generally u-shaped fastener portion, and an apertured retainer dimensioned for engaged reception of the fastener portion. Preferably the method comprises holding a plurality of the fastener portions, releasably holding a plurality of the retainers in positions opposite the fastener portions such that the apertures thereof face the pronged portions of the fastener portions, and sequentially driving the fastener portions of the two-part fasteners toward the retainers so as to cause the pronged portions to be engagably received within the apertures of the retainers. Preferably two rows of fastener portions and mating retainers are provided.

According to the method, body tissue to be fastened is positioned between the rows of fastener portions and retainers such that sequentially driving the fastener portions toward the retainers causes the fastener portions to be driven through the tissue so as to grip the tissue between the fastener portions and the retainers. The method further comprises cutting the tissue while driving the fastener portions toward the retainers.

The method is preferably accomplished on an apparatus which permits release of the tissue after the fastening and engagement of the two-part fasteners is complete.

BRIEF DESCRIPTION OF THE DRAWINGS

Preferred embodiments of the invention are described hereinbelow with reference to the drawings wherein:

FIGS. 13A, 13B, 13C and 13D are respectively, plan elevational, bottom, and cross-sectional views providing further details of the retainer holding cartridge;

DETAILED DESCRIPTION OF THE PREFERRED EMBODIMENTS

Figure 1:
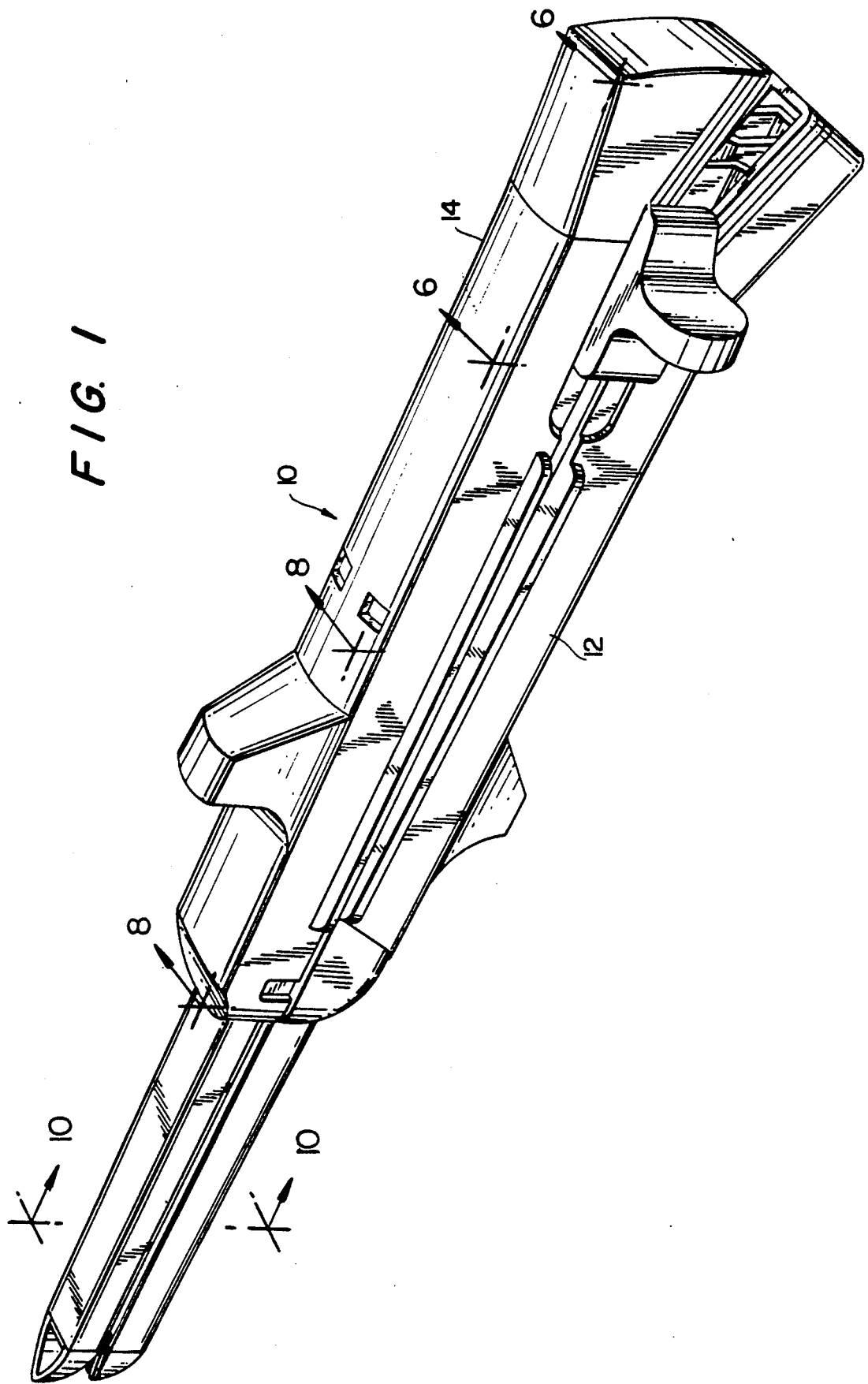
FIG. 1 is a perspective view of the apparatus for applying two-part surgical fasteners constructed according to the present invention.
Figure 2:
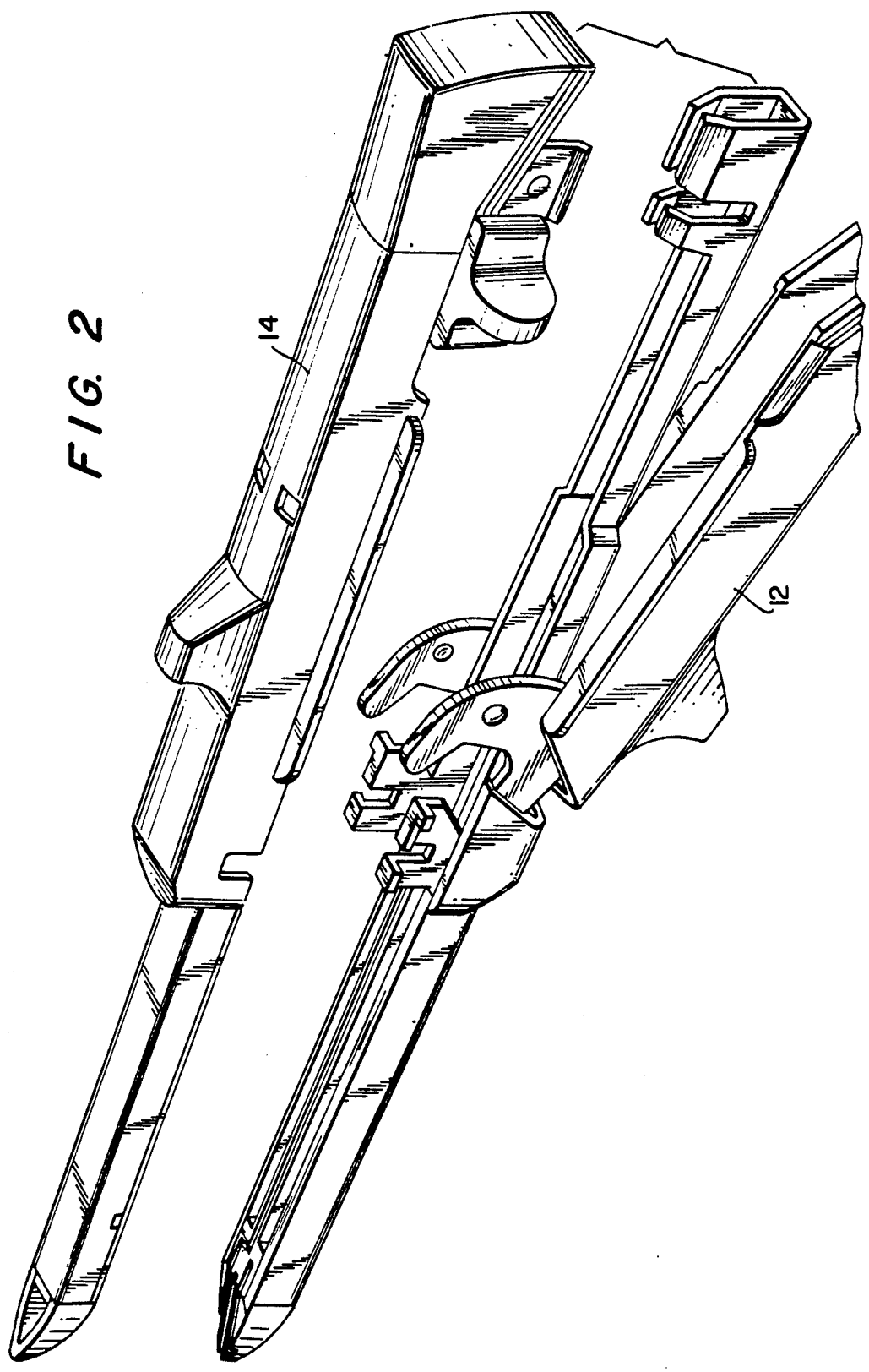
FIG. 2 is an exploded perspective view of the apparatus of FIG. 1, illustrating the two half sections of the fastener applying mechanism.

Referring initially to FIG. 1, there is illustrated a perspective view of the apparatus 10 for applying two-part fasteners constructed according to the present invention. The apparatus 10 includes half sections 12 and 14 as shown, which are adapted to be clamped together in a manner to be described. The two half sections 12 and 14 are shown in perspective view in FIG. 2 and each half section is shown with parts separated in FIGS. 3 and 4.

Figure 3:
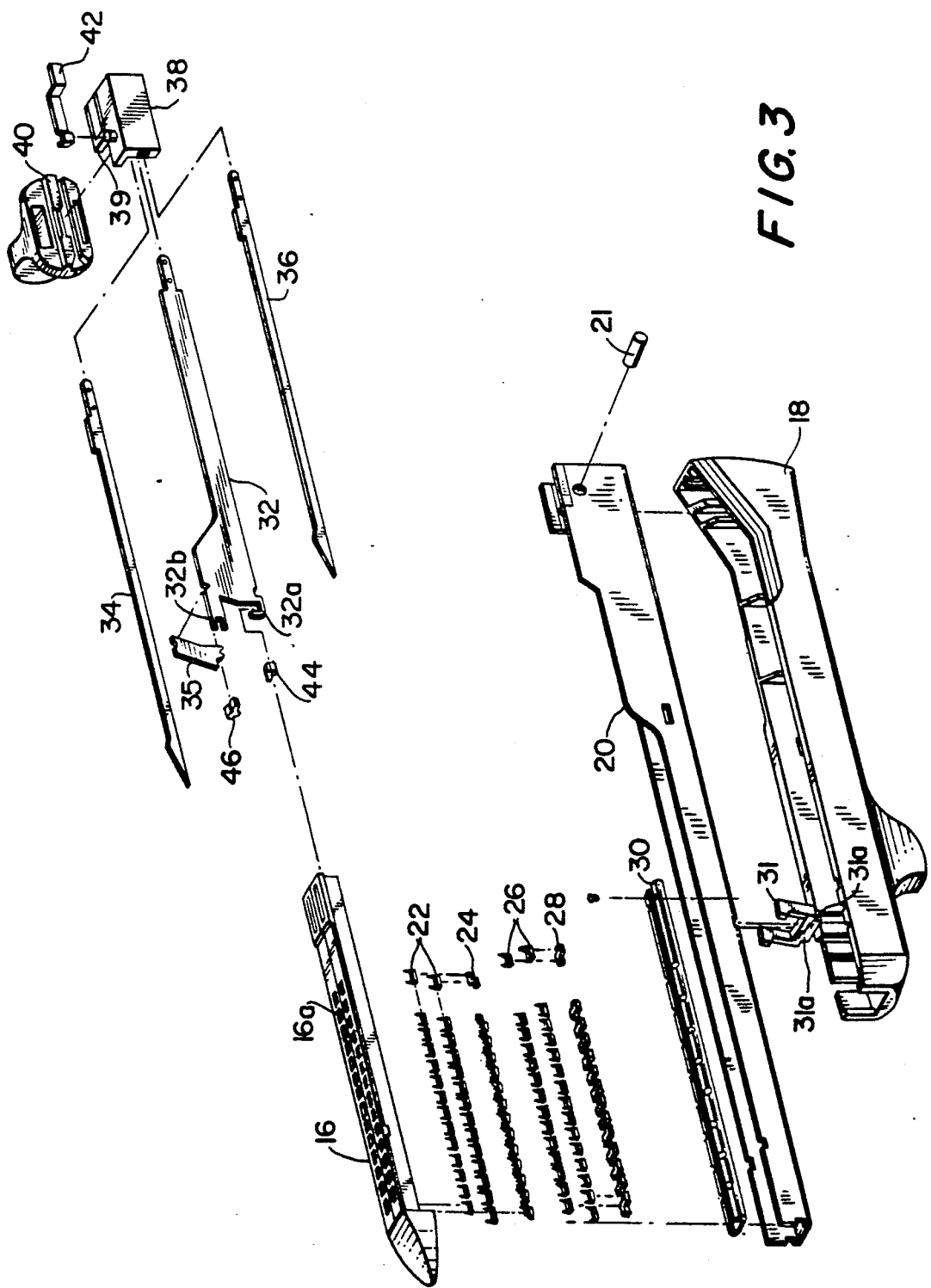
FIG. 3 is an exploded perspective view with parts separated, of the fastener cartridge and associated handle mechanism.

Referring now to FIG. 3, half section 14 for receiving and supporting fastener cartridge 16 is shown. The handle section includes body 18, which receives fastener channel 20. Fastener cartridge 16 receives two staggered rows of U-shaped fasteners. A first pair of rows of fastener portions such as fasteners 22 is disposed on one side of a knife bar 32 and is provided with corresponding fastener pushers 24. A second similar string of a pair of U-shaped fasteners 26 are advanced by corresponding pushers 28 on the other side of knife bar 32. Fasteners 22 and 26 are maintained within suitable spaces 16a provided in cartridge 16 which are dimensioned to frictionally support the fasteners until ejected by the pushers. Shoe plate 30 is provided as shown for slidable reception of a fastener shoe 44.

Referring further to FIG. 3, knife bar 32 is flanked by cam bars 34 and 36 which are connected to bar retainer 38 which in turn is connected to finger pad 40 for finger operated motion of the cam bars 34,36. A retainer or anchor 31 is provided for engagement with the pivoted handle of the retainer half section (to be described below) to retain the apparatus in the locked condition when the handle is closed. Fastener shoe 44 is attached to knife bar 32 at tab 32a on the fastener side and retainer shoe 46 is attached to knife bar 32 at tab 32b on the retainer side as shown. As will be described in further detail, fastener shoe 44 and retainer shoe 46 slide within respective shoe plates 30,50 (FIGS. 3 and 4) and serve to secure the two half sections 12,14 together after the knife bar is advanced a predetermined amount in order to prevent separation of the half sections. Also, the shoes 44,46 and the shoe plates serve to control the gap between the fastener cartridge and the retainer cartridge and thus the relative positions of the fastener portion and the retainer portion. Knife 35 having a sharp knife edge is attached to knife bar 32 as shown for cutting tissue simultaneously with the fastening operation. Knife 35 lags the cam bars a small distance, i.e. about 5 mm.

Figure 4:
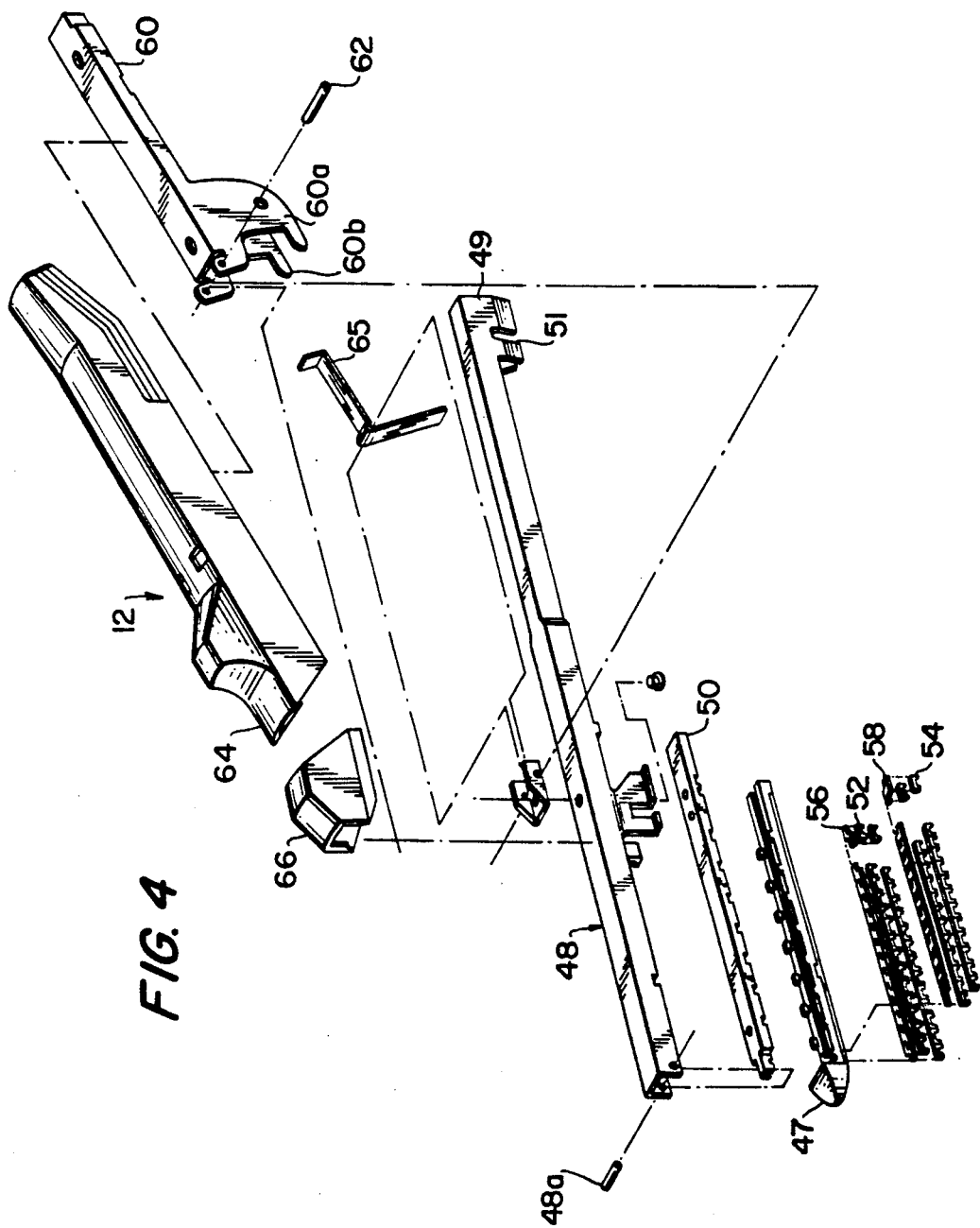
FIG. 4 is an exploded perspective view with parts separated, of the retainer cartridge and associated handle mechanism.

Referring now to FIG. 4 the retainer half section 12 is illustrated with parts separated. Retainer channel 48 is provided with retainer shoe plate 50 and retainer cartridge 47 for supporting two staggered rows of retainers 52 and 54, with associated retainer holders 56 and 58. The retainers are each precisely positioned opposite a respective fastener when the half sections of the apparatus are assembled.

Handle clamp 60 is pivotally attached to channel 48 via pin 62 with leaf spring 65 positioned therebetween to resiliently bias handle clamp 60 away from retainer channel 48. Handle cap 64 is attached to handle clamp 60 and nose cap 66 is provided as shown at the distal end of cap 64.

Figure 5:
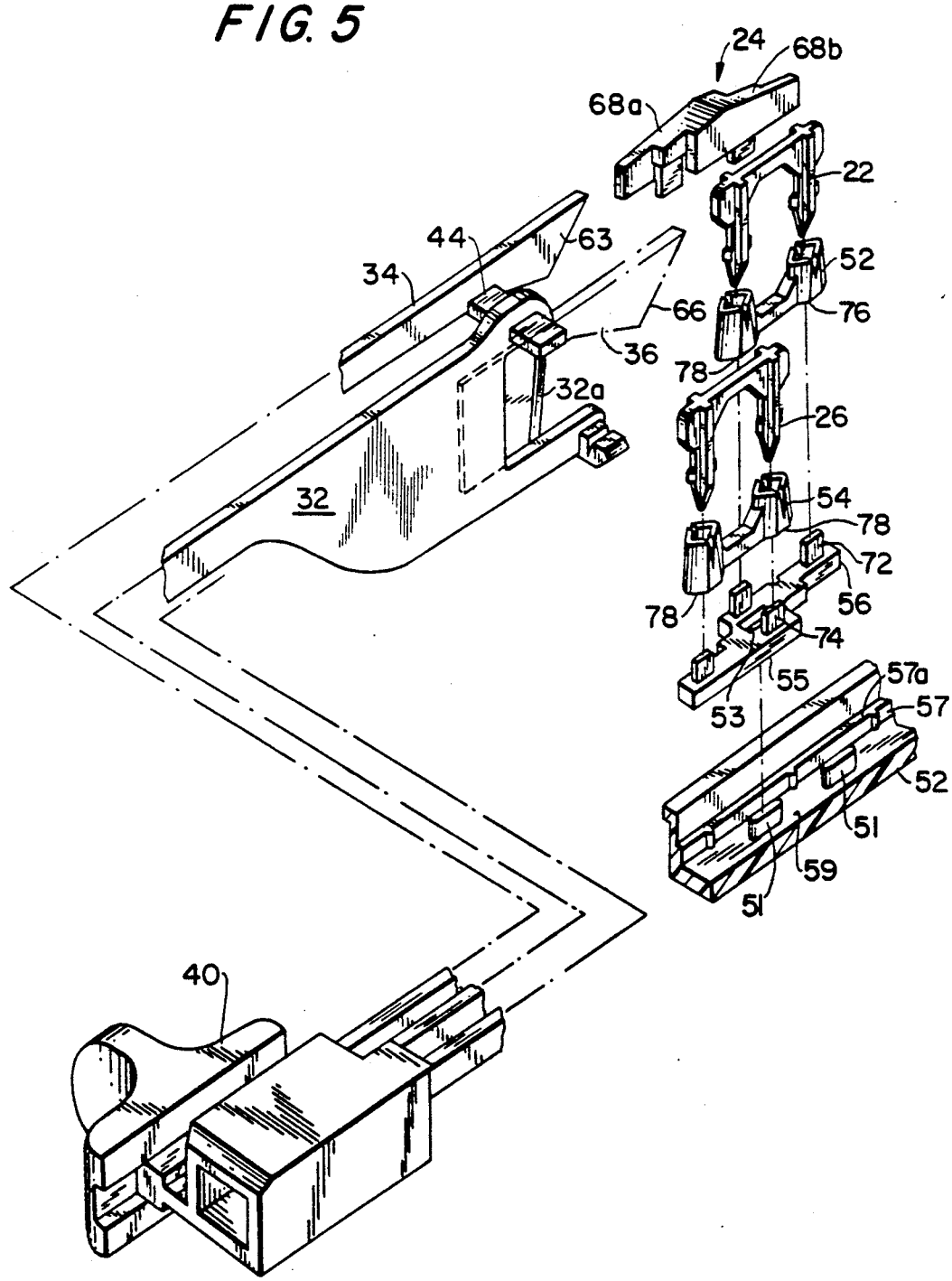
FIG. 5 is an exploded perspective view of the operable portions of the apparatus of FIG. 1, illustrating the mechanism for advancing camming fingers and a tissue cutting blade to secure the two part fastener/retainer and for cutting adjacent tissue.
Figure 10:
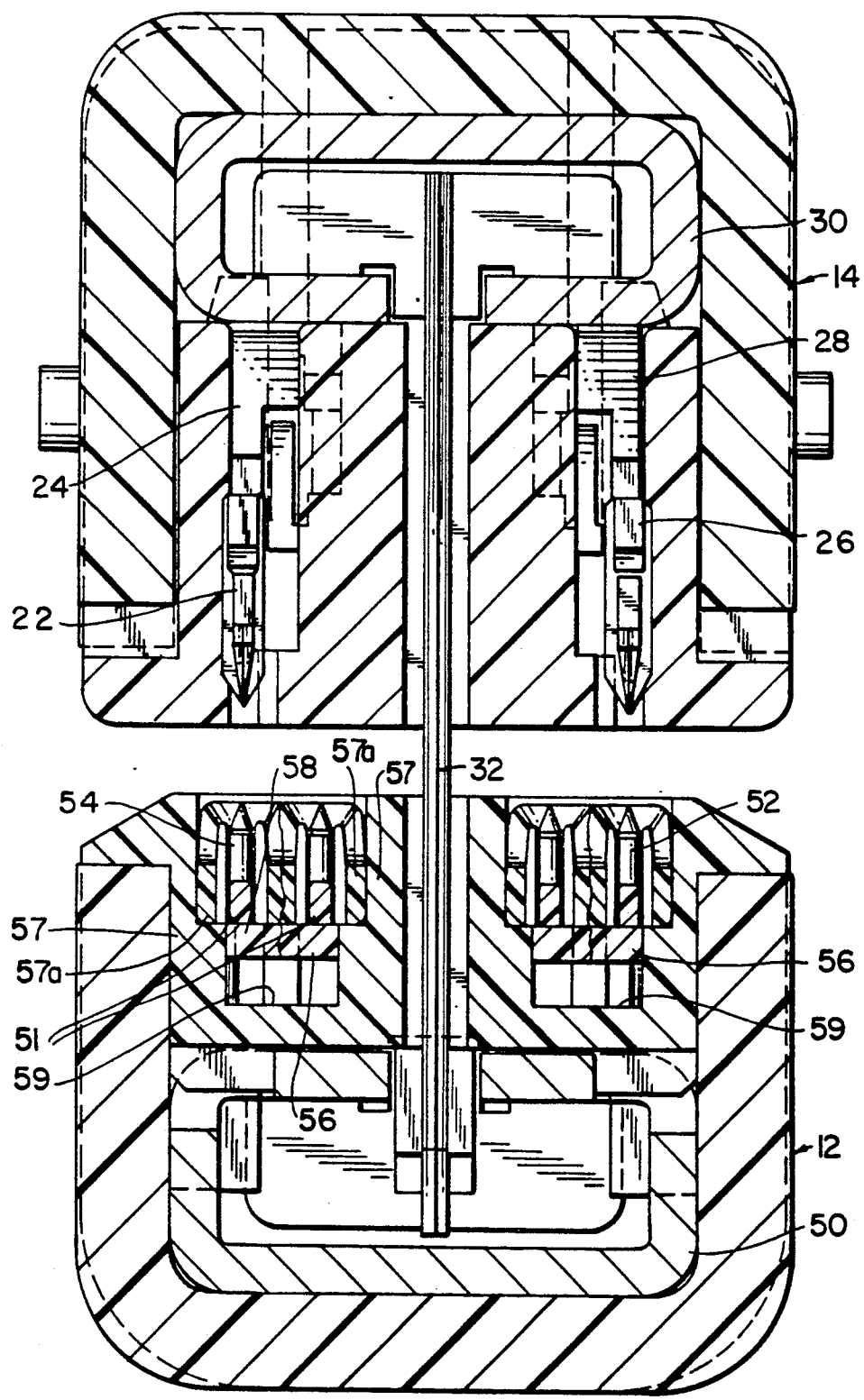
FIG. 10 is a cross-sectional view taken along lines 10—10 of FIG. 1, illustrating the relative positions of the fasteners and retainers prior to firing the apparatus.

Referring now to FIG. 5, the motion of knife bar 32 and associated cam bars 34,36 is illustrated. When finger pad 40 is moved distally by the surgeon, the distal sloped surfaces 63,66 of cam bars 34,36 engage the corresponding proximal surfaces 68a and 70a (not shown in FIG. 5) of fastener pushers 24 and 28 (not shown in FIG. 5), causing movement of the pushers in a direction substantially perpendicular to movement of cam bars 34, 36 and engagement with fasteners 22 and 26. This movement causes the fasteners to move transversely toward corresponding retainers which are at this time, secured in upstanding relation to retainer monitoring elements shown as retainer holders 56 and 58 (holder 58 not shown in FIG. 5) by insertion of upstanding posts 72,74 into the apertures 76,78 on the side of retainers 52,54 opposite the fastener side. Similarly, the retainer holders 56,58, prior to firing the fasteners, are positioned within cartridge 47 such that the top surfaces of the posts 72,74 are approximately at the level of the surfaces 57a of the side rails 57 of retainer cartridge 47 as shown in FIGS. 5 and 10. The retainer holders 56,58 are dimensioned to be positioned between rails 57 of the cartridge 52 with slight frictional fit to maintain the position shown in FIG. 10. This position permits the movement of holder 55 toward the lower surface 59 of cartridge 52 during firing such that posts 51 enter central apertures 53 of the holders 56 to assist in continued alignment of the fastener retainers 26 with the fasteners 27. Additional details relating to the fasteners and retainers will be provided in conjunction with FIGS. 12-17.

Figure 6:
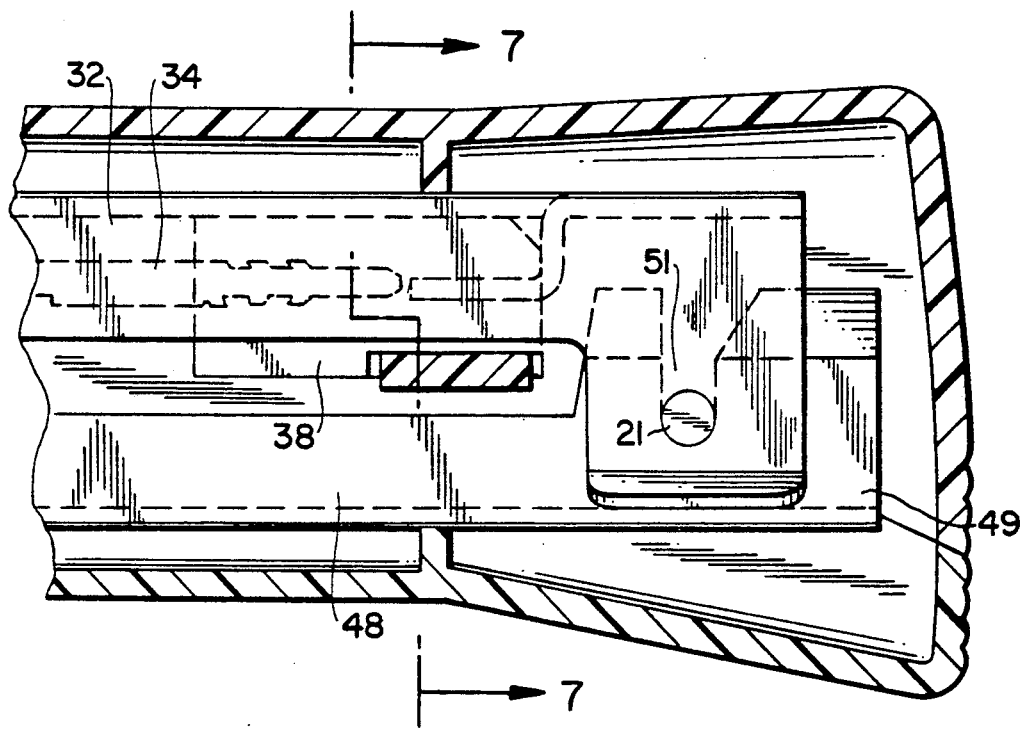
FIG. 6 is a view, partially in cross-section, taken along lines 6—6 of FIG. 1 illustrating the finger operated pad and related mechanism for advancement of the tissue cutting knife and fastener closure cam bars.
Figure 7:
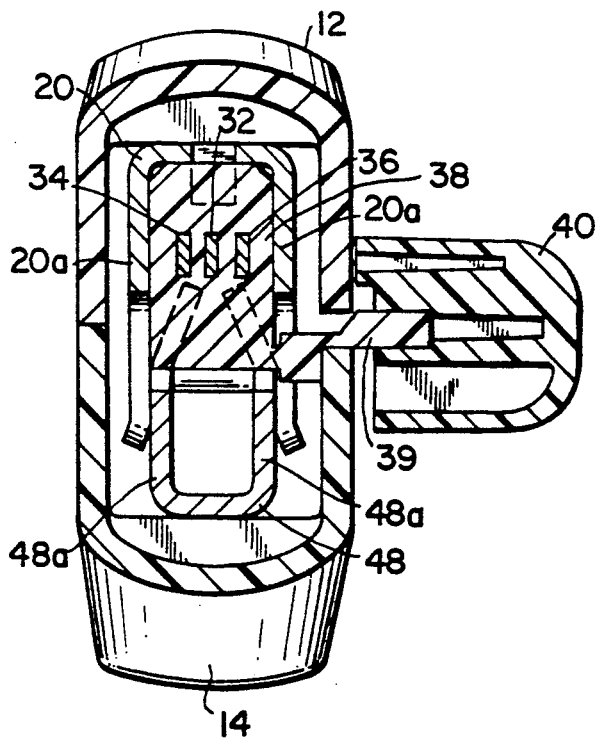
FIG. 7 is a cross-sectional view taken along lines 7—7 of FIG. 1 illustrating the finger operated advancement mechanism for cutting tissue and effecting closure.

Referring now to FIGS. 6 and 7 the finger operated pad and associated mechanism for advancing the tissue cutting knife and fastener closure cam bars are shown. FIG. 6 is a cross-sectional view taken along lines 6—6 of FIG. 1, and FIG. 7 is a cross-sectional view taken along lines 7—7 of FIG. 6. Pad 40 is connected to bar retainer 38 by stem 39 with cam bars 34,36 and knife bar 32 connected at their proximal end portions to bar retainer 38 (see also FIG. 3). The proximal end portion 49 of retainer channel 48 has a cut-out portion 51 (FIGS. 4 and 6). A pin 21 is inserted in fastener channel 20 and positioned within cut-out portion 51 to facilitate alignment of the retainer channel 48 with fastener channel 20 as shown in FIG. 6. Further alignment of the half sections 12, 14 of the apparatus is provided by the side walls 20a, 48a of the channels 20,48, respectively, as shown in FIG. 7, wherein the side walls 48a of channel 48 are slidably and snugly positioned within sidewalls 20a of channel 20 when the half sections 12, 14 of the apparatus are assembled.

Figure 8:
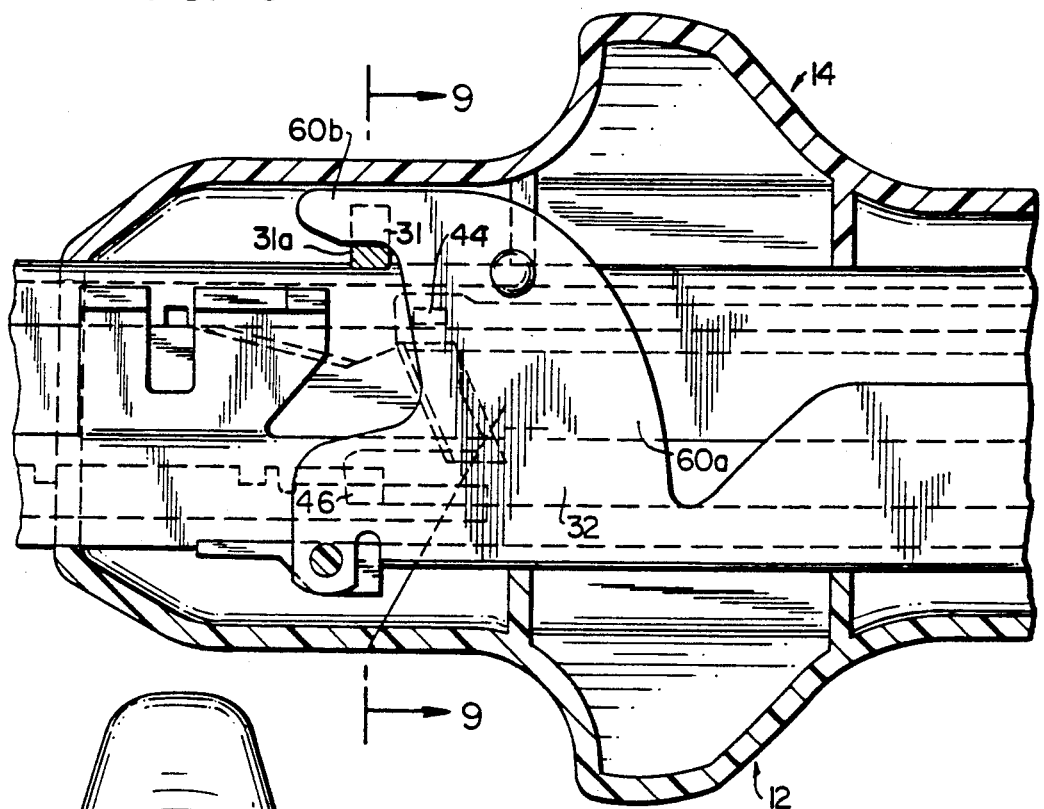
FIG. 8 is a view, partially in cross-section, taken along lines 8—8 of FIG. 1, illustrating the attachment mechanism for securing the two half sections of the apparatus together.
Figure 9:
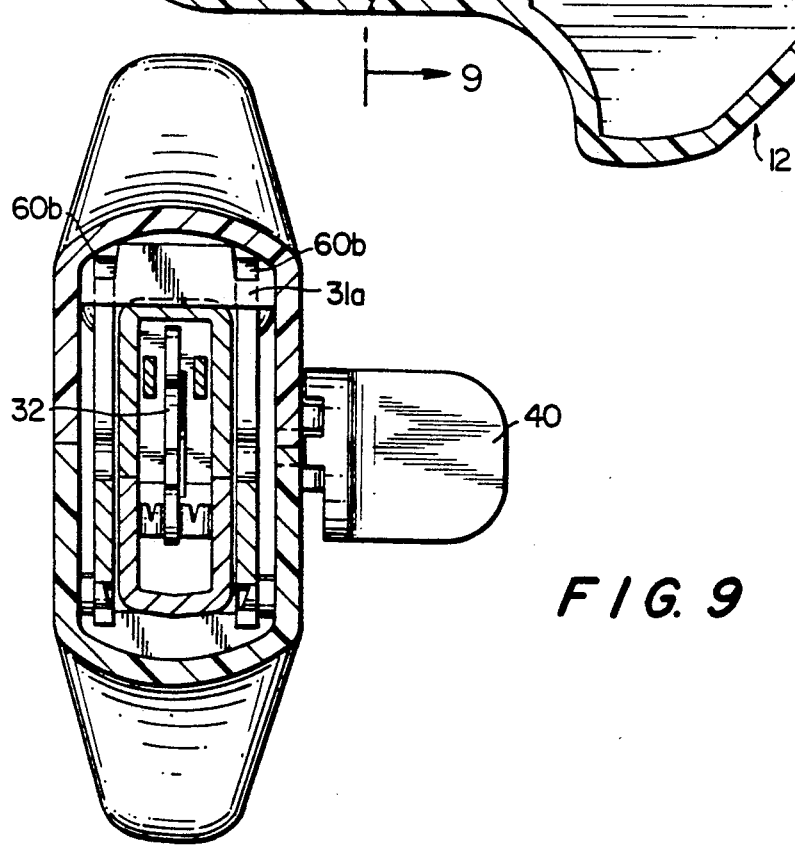
FIG. 9 is a cross-sectional view taken along lines 7—7 of FIG. 8, illustrating the attachment mechanism of FIG. 8.

Referring now to FIG. 8, the mechanism for locking the half sections 12,14 is illustrated in cross-section. Handle clamp 60 (shown in FIG. 4) is pivotally mounted to retainer channel 48 as described previously, and includes distal clamp section 60a having locking fingers 60b. These locking fingers are dimensioned and configured to engage shoulders 31a of anchor 31 attached to fastener channel 20 (also see FIG. 3) when the half sections 12,14 are assembled in face to face relation and handle 64 and clamp 60 are pivotally advanced toward half section 14. This movement causes engagement between locking fingers 60b and shoulders 31a of anchor 31 to secure the half sections 12,14 together.

Referring now to FIG. 8, a safety feature of the present apparatus is illustrated. The knife bar 32 includes fastener shoe 44 attached to the distal end portion 32a as shown, and retainer shoe 46 attached to the distal end portion 32b as shown (also, see FIG. 3). When the half sections 12,14 are fully assembled and handle 64 and clamp 60 are closed distal movement of finger pad 40 is made possible, causing corresponding distal movement of cam bars 34,36 and knife bar 32. With this motion, retainer shoe 46 and fastener shoe 44 slide distally within the respective channels defined by fasteners shoe plate 30 and retainer shoe plate 50. It will be readily appreciated that any distal movement of finger pad 40 will cause the shoes 44,46 to enter their respective channels and prevent separation of the half sections 12,14 in the event handle 64 and clamp 60 are inadvertently urged toward the unlocked position. Continued distal motion results in transverse movement of fastener pushers to cause sequential closure of the fasteners with the retainers.

Figure 11:
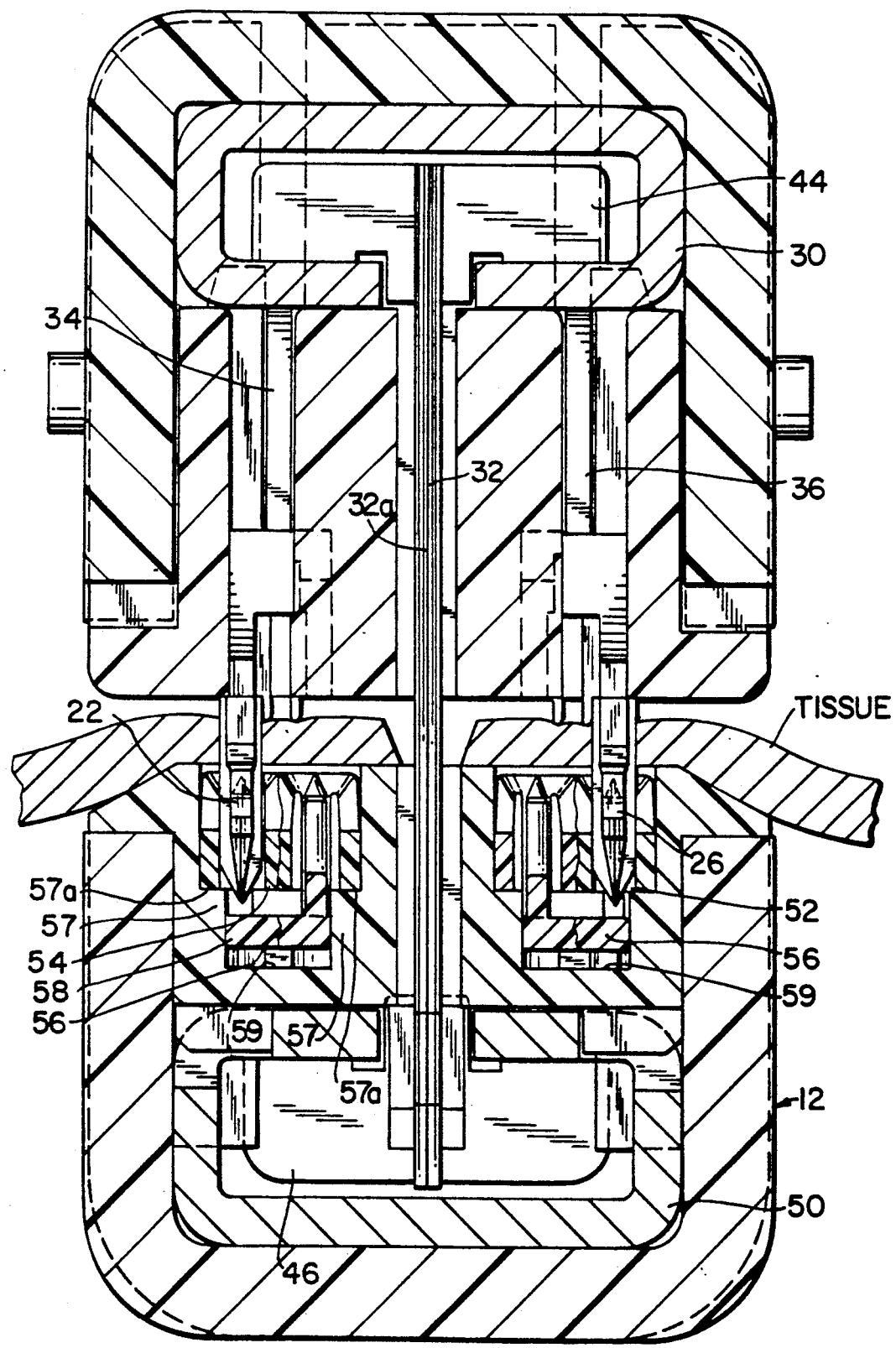
FIG. 11 is a view similar to FIG. 10, illustrating the fasteners and retainers after firing the apparatus.
Figure 12:
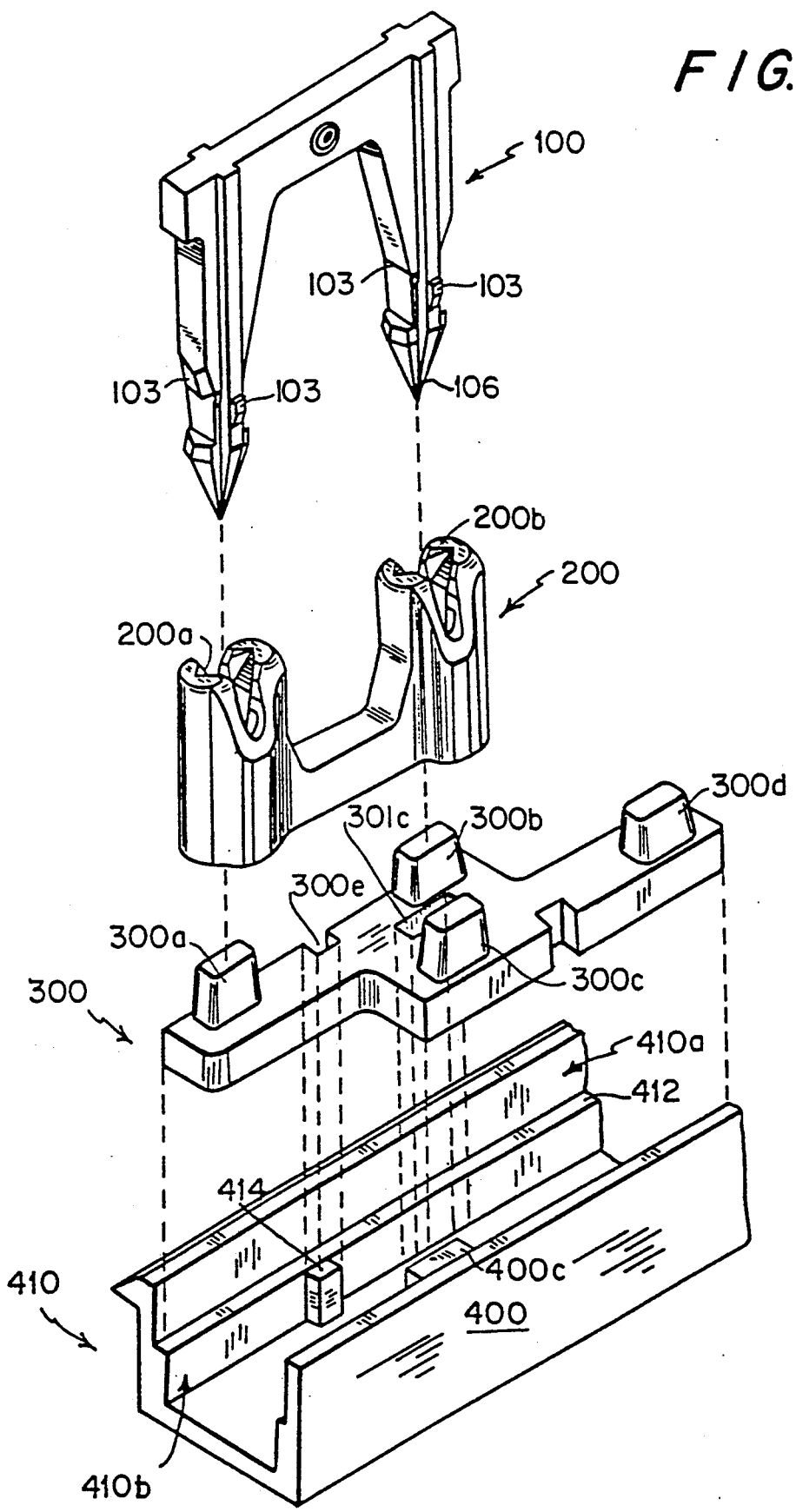
FIG. 12 is a more detailed exploded perspective view of a two-part surgical fastener shown with the retainer mounting element and the retainer holding cartridge of the present invention.
Figure 13D:
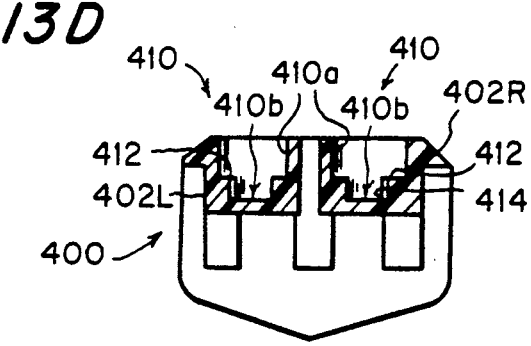

FIG. 10 illustrates the half sections 12,14 in the pre-fired positions and FIG. 11 illustrates the half sections 12,14 of the apparatus after the fasteners are fired and the tissue is cut. As can be seen the tissue is gripped by the half sections 12 and 14. Similarly, FIGS. 12, 13 and 14 illustrate the fastener and retainer system in exploded view. Referring now to FIG. 10 in conjunction with FIGS. 1 and 2, a cross section of the fastener system illustrates fastener half section 14 with exemplary fastener 22 and half section 12 with exemplary retainer 54. Retainer holder 58 secures retainer 54 in precisely correct aligned position by insertion of posts 51 into the apertures of the retainer on the side opposite the fastener entry side. FIG. 11 illustrates the half sections shown in FIG. 10 after firing the finger activated finger pad 40 which cause the following simultaneous actions:

1) knife 32a cuts tissue as shown.
2) fastener cam bars 34, 36 sequentially engage fastener pushers 24, 28 causing movement of the fasteners 22, 26 toward retainers 52, 54 such that the fasteners engagably enter the retainer openings and simultaneously push retainer holders 56 deeper into the cartridge 50 while releasing the hold which holders 56 previously had on retainers 52, 54. This position causes the resilient spear shaped leading edge of the absorbable two part fasteners 22,26 to be securely retained within the retainers 52, 54 which are dimensioned and shaped for corresponding locked interference fit with the fasteners. While this fastening action occurs the retainers 52,54 are supported on surfaces 57a of side shelves—or rails—57 as shown in FIG. 11. Thus, the tissue halves become securely fastened by the dual staggered rows of fasteners on each side of the cut and the organs are joined to form a single hollow chamber.

The downward motion of the fasteners is aligned precisely with the retainer openings due to the alignment of the retainers as secured by the holders 54 and the uniform downward motion provided by the fastener pushers 24. The second (or distal) sloped surface 68b of the same pusher, as shown in FIG. 4 facilitates proximal movement of cam bars 34,36.

Referring now to FIGS. 12-17, the inventive fastener and retainer system constructed according to the present invention is shown in exploded perspective views providing additional details of the fastener locking systems. For convenience of illustration in connection with these Figs., the numerals of the components shown in FIGS. 12 et seq. are numbered, beginning with 100. Thus, certain elements in these Figs. will bear numerals differing from those utilized in the previous Figs.

Referring to FIG. 12, fastener 100 has a spear shaped tip 106 dimensioned for forced entry into apertures 200a and 200b of retainer 200. Bumps 103 help to retain fastener 100 within retainer 200 after entry has been completed. In FIG. 12 bumps 103 are shown at two locations. Bumps 103 are also provided on the rear face of fastener 100 (not shown) to retain the fastener. Retainer 200 is securely positioned on retainer holder 300 having upstanding posts 300a, 300b, 300c, 300d which are dimensioned and configured to enter apertures 200a and 200b of retainers 200 on the side opposite the fastener entry side. The retainer holder 300 provides a stable flat base for the retainer and disengages from the retainer when the fastener portion engages the retainer. As noted hereinabove, during the operation of the instrument the fasteners are ejected from the fastener holding cartridge to mate with their respective retainers. Further details of novel retainer holding cartridge 400 may be seen by referring to FIGS. 13a, 13B, 13C and 13D.

Retainer holding cartridge 400 is an elongated piece having two members 402L and 402R longitudinally extending proximally from the distal end 404 of the retainer holding cartridge 400. Left and right members 402L and 402R define a center longitudinal slot 406 for receiving the distally moving knife member 32 described hereinabove. In one embodiment, the proximal ends of members 402L and 402R have outwardly projecting pins 408L and 408R respectively, for pivotally mounting to a surgical fastener applying instrument. Alternatively, these pins could be eliminated. Each member 402L and 402R has a compartment 410 comprising a relatively wide upper vertical walled channel 410a for seating one or more retainers, and a relatively narrow vertical walled lower channel 410b for mounting the retainer mounting elements. The difference in widths between the upper and lower channels defines shelves 412 on both sides of the compartment which support the retainers and act as a backstop. The lower channel 410b is adapted to hold retainer holders 300 in a frictional fitting such that they are frictionally supported in an initial upper position wherein the retainer holders 300 are engaged with the retainers 200. The retainer holders 300 are downwardly slidable when forced out of engagement with the retainers 200 by the entering prongs of the fastener portions 100. Vertical guide rails 414 on the sides of the channels cooperate with slots 300e formed in retainer holder 300 to reduce the unwanted torquing of the retainer holders 300 and prevent the retainer holders 300 from moving distally or proximally. In the alternative, vertical post 400c may be provided to engage an aperture 301c in the retainer holder 300. See, also, post 51 engaging aperture 53 as shown in FIG. 5. Alternatively, the retainer cartridge 400 could be provided with both a vertical guide rail 414 on each side to engage a respective side slot 300e in retainer holder 300, and a central post 400C as shown in FIG. 12 dimensioned to be received in aperture 301C in retainer holder 300.

Figure 14A:
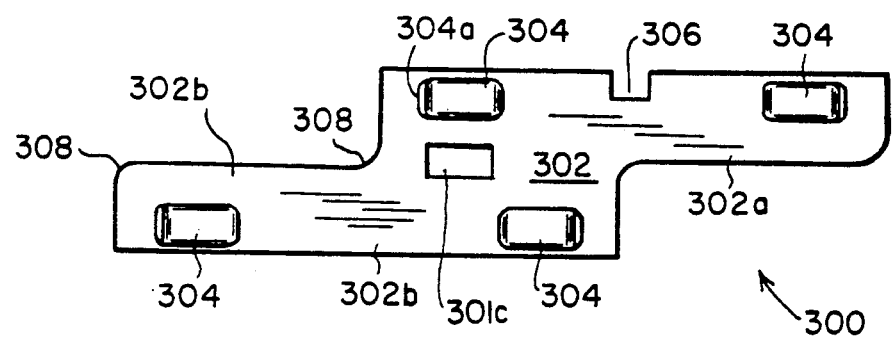
FIGS. 14A and 14B are plan views of left hand, and right hand retainer mounting elements, respectively.
Figure 14B:
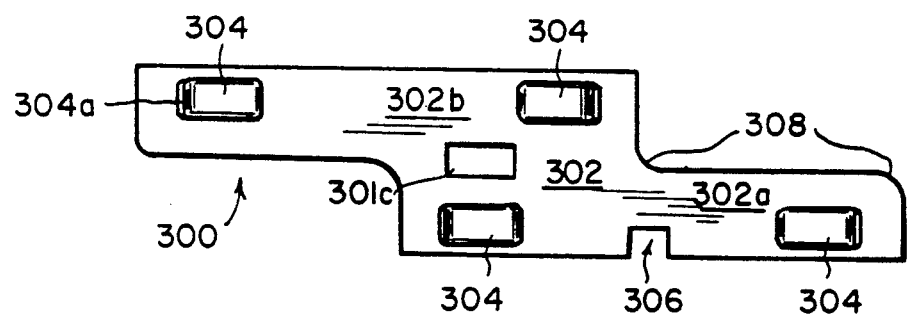
Figure 15:
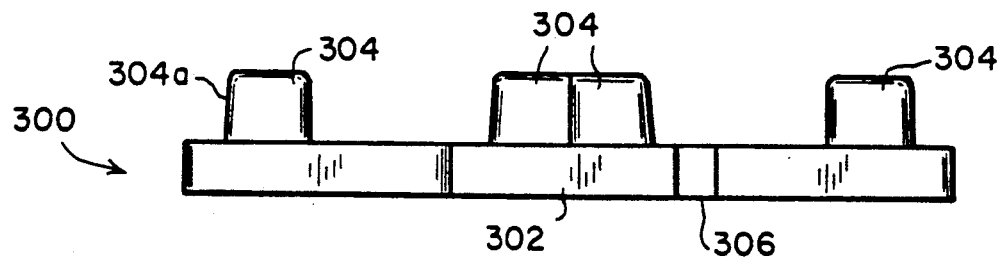
FIG. 15 is a side elevational view of the retainer mounting element of FIG. 14B.

Referring now to FIGS. 14A, 14B and 15, further details of the retainer holders are shown. Retainer holder 300 includes a base 302 having two integrally connected substantially rectangular portions 302a and 302b, and a plurality of upright posts 304 for entry into the apertures on the bottom portion of the retainer as described hereinabove. The base has a vertical notch 306 for slidably engaging guide rails 414 of the retainer cartridge 400. Rounded corners 308 enable a smoother sliding fit between the convex corner of one retainer mounting element being adapted to fit into the concave corner of another mounting element. As noted, the width of base 302 is such that the retainer mounting element 300 is retained in the lower channel 410b by friction, or slight interference fit, although the retainer mounting element 300 is slidable in the vertical direction. The uprights 304 ideally each have a sloped side 304a which is angled slightly off the vertical such that the top of the upright is slightly narrower than the bottom. The tapering facilitates the entry and removal of the uprights from the retainer apertures.

Figure 16A:
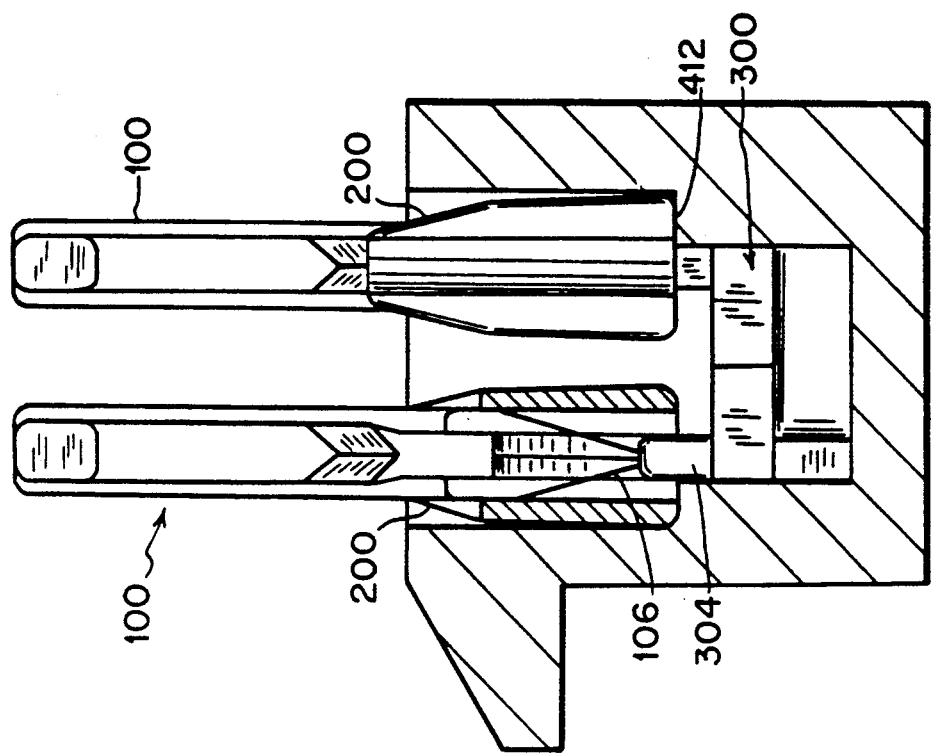
FIG. 16A illustrating in cross-sectional view, further details of the retainer portion of a two-part surgical fastener positioned on a retainer mounting element in the pre-fired position.
Figure 16B:
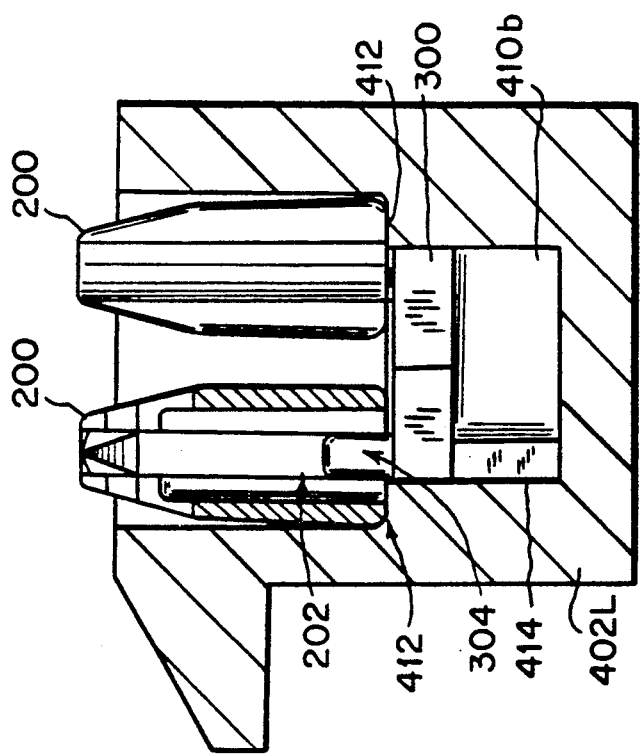
FIG. 16B illustrates in cross-sectional view, the retainer portion of a two-part surgical fastener positioned on a mounting element in the fired position.
Figure 17:
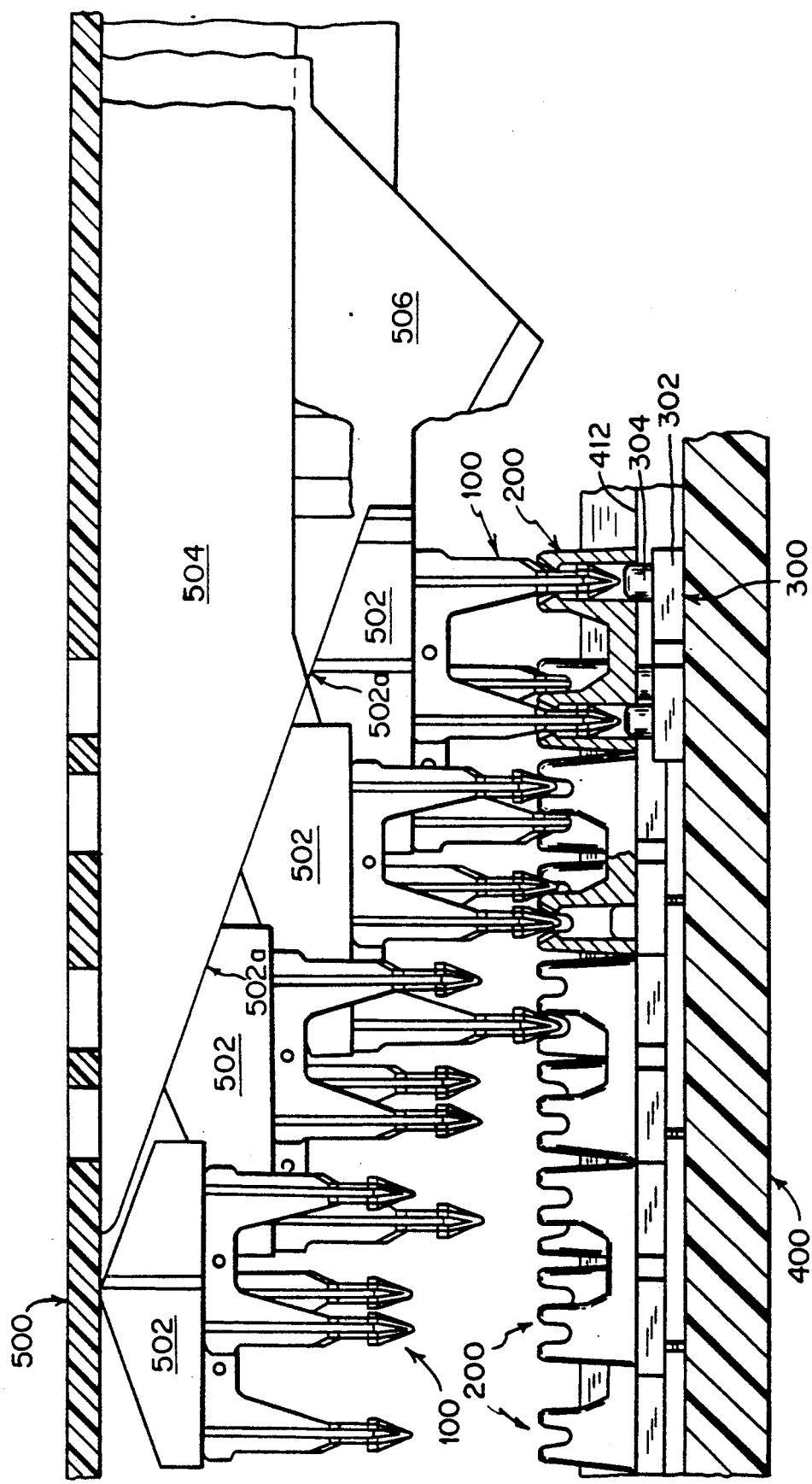
FIG. 17 illustrates in cross-sectional view, the two part surgical fasteners being joined in an apparatus employing the present invention.

Referring now to FIGS. 16A, 16B and 17, the retainers 200 are initially in the position illustrated in FIG. 16A. The retainer 200 is located in the upper chamber 410a, and mounted on retainer holder 300 by means of uprights or posts 304 which are inserted into the apertures 02 at the bottom of the retainer 200. A portion of the bottom of the retainer 200 overlaps the edge of base 302 such that the overlapping portion rests on shelf 412.

Retainer holder 300 is slidably mounted within the lower channel 410b of the cartridge 400 with notches 300e and 306 in engagement with guide rail 414.

When the fasteners 100 are inserted into retainers 200, the barbed tips 106 of the fasteners push down on the uprights 304, thereby pushing the retainer mounting element 300 down into a position where it is no longer in engagement with the retainer 200. The retainers 200 are supported by shelves 412 such that they are braced against downward movement. Upon disengagement with the retainer holders 300, the retainers 200 are free to be lifted out of the cartridge 400 in engagement with the fasteners.

FIG. 17 illustrates in further detail, the operative portion of the apparatus for applying surgical fasteners, employing the fastener and cartridge system of the present invention as described hereinabove. The fastener holding cartridge 500 contains fastener pushers 502, cam bar 504, and optionally a knife 506. When actuated, the cam bar 504 is moved distally, thereby contacting the sloped camming surface 502a of pusher elements 502 and urging the fastener portions downward into the retainer cartridge 400 where fastener 100 engages its respective retainer 200. As described above, the cam bar 504 operates upon the pusher elements 502 sequentially, first contacting the proximal end of each pusher element. As noted, because of this movement there may be a tendency for unwanted torque to develop which might otherwise cause a relative clockwise pivoting of the fastener. Flat mounting element bases 302 and shelves 412 help insure that the retainers 200 do not pivot appreciably.

In use, the apparatus is positioned such that a layer of body tissue is situated between the fastener holding cartridge 500 and the retainer holding cartridge 400. When the apparatus is actuated the fastener barbs 106 will penetrate the tissue layer and lock into the retainer 200, thereby sealing the tissue. Although FIG. 17 shows the fasteners 100 moving downwardly, the direction of movement to engage retainer 200 will obviously depend upon the orientation of the apparatus during use.

The apparatus as described hereinabove is preferably constructed as a disposable apparatus suitable for a single use. However, the apparatus is readily adaptable to a multiple use or non-disposable form merely by structuring the fastener and retainer cartridges so as to be replaceable within their respective channels. In such case, replacement of the knife bar 32 with knife blade 35 is also desirable in order to assume precise and accurate cutting of the tissue. The cam bars 34,36 could also be replaceable along with knife 32. In the preferred form, the components are constructed of steel except for the cartridges, and the finger pad 40 which are constructed of a suitable plastic material such as nylon or polycarbonate. The preferred fastener and retainer are composed of a bioabsorbable polymeric material, such as polymers or copolymers of glycolide, lactide, p-dioxanone, polyester, polyamino acids and the like, the preferred construction of which is shown and described in U.S. Pat. No. 4,932,960, which is hereby incorporated by reference.

What is claimed is:

1. Apparatus for applying at least one row of two-part surgical fasteners, each surgical fastener having a fastener portion and a retainer, which comprises:
   a) means for holding said fastener portions of said two part surgical fasteners;
   b) a retainer cartridge having means for holding a plurality of retainers in positions opposite said fastener portions;
   c) a plurality of retainer mounting elements located in said retainer cartridge for releasably engaging and holding said retainers; and
   d) means for sequentially driving said fastener portions of said two part fasteners into engagement with their respective opposed retainer.

2. The apparatus of claim 1 wherein the fastener portions and retainers are arranged in longitudinal alignment with the axis of the apparatus.

3. The apparatus of claim 2 adapted to fasten body tissue and further comprising means to cut the body tissue adjacent the location of application of said fasteners.

4. The apparatus of claim 1 wherein said retainer mounting elements are slidably mounted within at least one channel in the retainer cartridge.

5. The apparatus of claim 4 further comprising backstop means for bracing the retainers when engaging with the fastener portions.

6. The apparatus of claim 5 wherein said backstop means comprises a horizontal shelf portion of the cartridge upon which said retainers at least partially rest.

7. The apparatus of claim 6 wherein said retainer cartridge includes lower and upper channels having vertical side walls, and wherein the lower channel is of lesser width than the upper channel and located below said upper channel thereby forming at least one shelf portion.

8. The apparatus of claim 7 wherein said lower channel has a plurality of vertical guide rails and said retainer mounting elements each have at least one vertical notch for cooperating with a respective one of said vertical guide rails.

9. The apparatus of claim 1 wherein said retainer mounting elements release their respective retainers in response to the engagement of the fastener portions with their respective retainers.

10. The apparatus of claim 1 wherein the retainer mounting elements each comprise a base portion and at least one upright post for engaging an aperture in the retainer and frictionally holding said retainer.

11. The apparatus of claim 10 wherein a surface portion of said upright post is inclined on at least one vertical side.

12. The apparatus of claim 1 wherein said two-part surgical fastener portions are bio-absorbable.

13. Apparatus for applying at least one row of two-part surgical fasteners to body tissue, each surgical fastener having a fastener portion and a retainer dimensioned and configured to receive the fastener portion into engaged relation therewith, which comprises:
   a) means for releasably holding a plurality of said fastener portions;
   b) means spaced from said fastener holding means for releasably holding a plurality of said retainers in positions opposite the respective fastener portion; and
   c) means for sequentially advancing each said fastener portion toward said retainers so as to cause said fastener portion to engage said retainers while fastening body tissue therebetween.

14. Apparatus for applying at least one row of two-part surgical fasteners to body tissue, each surgical fastener having a pronged fastener portion for piercing body tissue, and an apertured retainer dimensioned and configured for engaged reception of said pronged fastener portion in interference fit therewith for gripping the body tissue therebetween which comprises:
   a) means for holding a plurality of said fastener portions in generally aligned relation;
   b) means spaced from said fastener portion holding means for gripping body tissue therebetween and for releasably holding a plurality of said retainers in generally aligned relation and positioned opposite said fastener portions when the body tissue is positioned therebetween; and
   c) means for sequentially advancing said pronged fastener portions toward said aperture retainers to cause said fastener portions to pierce the body tissue and to be received within the apertures of said retainers in engaged interference relation so as to cause said fastener portions and said retainers to be engaged while gripping the body tissue therebetween.

15. Apparatus for applying at least two rows of two-part surgical fasteners to body tissue and for cutting the body tissue, each said surgical fastener having at least two pronged fastener portion for piercing body tissue, and a retainer member dimensioned and configured to receive said fastener portion in engaged relation such that the fastener portion and the retainer member are respectively positioned on opposite sides of the body tissue, which comprises:
 a) a two part frame having separable sections capable of releasable attachment to each other and each having an elongated finger portion;
 b) a fastener carrying cartridge mounted along one of said finger portions and carrying a plurality of said fastener portions;
 c) a retainer carrying cartridge mounted along said other finger portion opposite said fastener cartridge and carrying a plurality of said retainer members positioned opposite said fastener portions, each said retainer member having apertures dimensioned and positioned for reception of said pronged portions of said fastener portions when said fastener portions are advanced toward said retainer members;
 d) means mounted on said frame for sequentially advancing said fastener portions toward said retainer members while piercing body tissue positioned therebetween to effect application of said two-part fasteners to the body tissue; and
 e) means associated with said fastener advancement means to cut body tissue adjacent the location of application of said fasteners.

16. The apparatus of claim 15 wherein said two-part frame comprises a pair of channel members having means to releasably attach said members in face to face relation.

17. The apparatus of claim 16 wherein said fastener cartridge comprises two pairs of rows of staggered apertures dimensioned and configured for frictionally holding a plurality of said fastener portions.

18. The apparatus of claim 17 wherein said retainer cartridge comprises a plurality of openings correspondingly dimensioned and positioned for holding a like plurality of fastener retainer members having fastener reception openings correspondingly positioned opposite said fastener members for inception of said pronged fastener portions therein when said fastener portions are advanced toward said retainer members.

19. The apparatus of claim 18 further comprising a plurality of retainer holders positioned in said retainer cartridge, said holders having means to support said retainer members in position for reception of said fastener portions.

20. The apparatus of claim 19 further comprising a plurality of fastener pushers positioned above said fastener portions on the side opposite said retainer members, said fastener pushers being dimensioned and positioned such that advancement thereof toward said fastener portions cause said fastener portions to engage said retainer members.

21. The apparatus of claim 20 further comprising a pair of cam bars positioned for slidable movement distally and proximally within said frame for sequential engagement with said fastener pushers, said cam bars being dimensioned and configured to sequentially advance said fastener pushers toward said fastener portions to effect engagement of said fastener portions with said retainer members.

22. The apparatus of claim 21 wherein each said fastener pushers has at least one camming surface for effecting movement thereof in a direction substantially perpendicular to the movement of said cam bars.

23. The apparatus of claim 22 wherein each said fastener, pushers has dual oppositely sloped surfaces.

24. The apparatus of claim 23 wherein means are provided in said retainer cartridge for releasably supporting said retainer members in upright position with respect to said fastener portions of said fasteners.

25. The apparatus of claim 24 wherein said retainer support means comprises a plurality of retainer support members having upright posts dimensioned for insertion into said apertures of said retainer members, said retainer support members being dimensioned to be frictionally supported within said retainer cartridge.

26. The apparatus of claim 25 wherein said retainer support upright posts are engagable by said pronged portions of said fastener portions during engagement of said fastener portions and said retainer members such that said fastener portions cause said retainer support members to be released from said retainer means during engagement of said fastener portions and said retainer means.

27. The apparatus of claim 26 wherein means is associated with said cam bars to prevent separation of said frame sections after said cam bars are advanced in the fastener advancement direction a predetermined distance.

28. The apparatus of claim 27 wherein said frame comprises a generally U-shaped shoe plate provided between each said fastener and retainer cartridge and the respective channel members of said frame.

29. The apparatus of claim 28 wherein each said shoe plate defines a channel for reception of a respective shoe associated with said cam bars, said respective shoes preventing separation of said frame members when said cam bars are advanced a predetermined distance due to the entry of said shoes associated therewith into said channels defined by said shoe plates.

30. The apparatus of claim 29 wherein said means to support said retainer members in position for reception of said fasteners comprises at least two side rails extending longitudinally of said retainer cartridge and dimensioned to interfere with downward movement of said retainers so as to support said retainers firmly during engagement with said fastener portions.

31. The apparatus of claim 15 wherein said fastener carrying cartridge is removable.

32. The apparatus of claim 31 wherein said retainer carrying cartridge is removable.

33. Method for applying at least one row of two-part surgical fasteners, each surgical fastener having a pronged fastener portion and a retainer, comprising:
 a) holding said fastener portions of said two-part surgical fasteners;
 b) releasably holding a plurality of retainers in positions opposite said fastener portions; and
 c) sequentially driving said fastener portions of said two-part fasteners into engagement with their respective opposed retainers.

34. Method for applying at least one row of two-part surgical fasteners, each surgical fastener having a pronged generally u-shaped fastener portion, and an apertured retainer dimensioned for engaged reception of said fastener portion, comprising:
 a) holding a plurality of said fastener portions of said two-part surgical fasteners;

b) releasably holding a plurality of said retainers in positions opposite said fastener portions such that the apertures thereof face the pronged portions of said fastener portions; and c) sequentially driving said fastener portions of said two-part fasteners toward said retainers so as to cause said pronged portions to be engagably received within said apertures of said retainers.

35. The method for applying at least one row of two-part surgical fasteners according to claim 34 further comprising positioning tissue to be fastened between said rows of fastener portions and retainers such that sequentially driving said fastener portions toward said retainers causes said fastener portions to be driven through the tissue so as to grip the tissue between said fastener portions and said retainers.

36. The method according to claim 35 further comprising cutting the tissue while driving said fastener portions toward said retainers.

37. The method according to claim 36 wherein said cutting step is performed between said two rows of said two-part fasteners.

38. The method of claim 37 wherein said tissue fastening step is accomplished on an apparatus which permits release of the tissue after the fastening and engagement of said two-part fasteners is complete.

39. The method of claim 36 wherein at least two pairs of parallel rows of fastener portions are held in position for fastening and at least two corresponding pairs of parallel rows of retainers are positioned opposite said fastener portions, and said cutting step is performed between said two pairs of parallel rows of fasteners.

40. The method according to claim 35 wherein at least two rows of said fastener portions are held in first positions, and at least two corresponding rows of said retainers are held in positions opposite said first two rows of fastener portions.

41. A method for applying at least two pairs of rows of two-part surgical fasteners to body tissue, each surgical fastener including a fastener portion having a U-shaped configuration having a pair of prongs and a mating retainer having a pair of members defining apertures for engaged reception of said prongs, comprising:

a) holding a plurality of said fastener portions in two pairs of spaced apart generally parallel rows on one part of a two-part apparatus;

b) releasably holding a plurality of said retainers in two pairs of correspondingly spaced apart generally parallel rows on a second part of said two-part apparatus in a manner such that said apertured members of said retainers face said pairs of prongs of said fastener portions when said two-part apparatus is assembled;

c) positioning tissue to be fastened between said respective two parts of said apparatus and locking said two parts together;

d) sequentially driving said fastener portions of said two-part fasteners toward said retainers by advancing fastener driving means sufficient to cause said pronged portions to be driven through the tissue and to be engagably received within said apertures of said retainer members while cutting the tissue generally medially between said rows of pairs of fastener portions, said fastener driving means preventing separation of said half portions of said apparatus during the step of driving said fastener portions; and e) withdrawing said fastener driving means so as to release said half portions of said apparatus to permit separation thereof for removal of the fastened tissue.

42. The method of claim 41 wherein said retainers are firmly supported on support means while driving said fastener portions into engagement therewith.

43. The method of claim 42 wherein said support means comprises at least two rails defining retainer support shelves and extending longitudinally of said apparatus.

* * * * *